United States Patent
Guo

(10) Patent No.: US 11,091,739 B2
(45) Date of Patent: Aug. 17, 2021

(54) REAGENT KIT FOR STEP-BY-STEP HUC-MSC CULTURE AND HUC-MSC ACQUIRED USING SAID REAGENT KIT

(71) Applicants: Lei Guo, Beijing (CN); Cheng Li, Beijing (CN)

(72) Inventor: Lei Guo, Beijing (CN)

(73) Assignees: Lei Guo, Beijing (CN); Cheng Li, Beijing (CN)

( * ) Notice: Subject to any disclaimer, the term of this patent is extended or adjusted under 35 U.S.C. 154(b) by 324 days.

(21) Appl. No.: 16/061,272

(22) PCT Filed: Dec. 11, 2015

(86) PCT No.: PCT/CN2015/097150
§ 371 (c)(1),
(2) Date: Jun. 11, 2018

(87) PCT Pub. No.: WO2017/096617
PCT Pub. Date: Jun. 15, 2017

(65) Prior Publication Data
US 2018/0362932 A1  Dec. 20, 2018

(51) Int. Cl.
*C12N 5/0775* (2010.01)

(52) U.S. Cl.
CPC ........ *C12N 5/0665* (2013.01); *C12N 2500/44* (2013.01); *C12N 2500/46* (2013.01); *C12N 2501/115* (2013.01); *C12N 2506/1369* (2013.01)

(58) Field of Classification Search
CPC .............. C12N 5/0665; C12N 2500/44; C12N 2506/1369; C12N 2501/115
See application file for complete search history.

(56) References Cited

FOREIGN PATENT DOCUMENTS

WO     WO2012148125 A1 * 11/2012 ............... C12N 5/02

OTHER PUBLICATIONS

English machine translation of WO2012148125A1. p. 1-10 (Year: 2012).*
Furue et al. Heparin promotes the growth of human embryonic stem cells in a defined serum-free medium. PNAS. vol. 105. No. 36, p. 13409-13414 (Year: 2008).*
Rajala et al. Testing of nine different xeno-free culture media for human embryonic stem cell cultures. Human Reproduction vol. 22, No. 5 pp. 1231-1238 (Year: 2007).*
11140—MEM non-essential amino acids. Technical Resources. ThermoFisher Scientific, p. 1 (Year: 2015).*

* cited by examiner

*Primary Examiner* — Taeyoon Kim
(74) *Attorney, Agent, or Firm* — Lewis Roca Rothgerber Christie LLP

(57) ABSTRACT

A serum-free culture method for human umbilical cord mesenchymal stem cells (hUC-MSC), said method using a step-by-step method to culture hUC-MSC: first using a TME culture medium for culturing for 3-4 hours to promote hUC-MSC adherence, and then switching to a TMD culture medium for rapid amplification.

7 Claims, 9 Drawing Sheets

1A    1B    1C 2A    2B 2C    2D

2E 3A    3B    3C 4A    4B    4C 5A    5B    5C

6A

6B

6C

6D

6E

6F

6G

6H

6I

7A

7B

7C 8A
8B

REAGENT KIT FOR STEP-BY-STEP HUC-MSC CULTURE AND HUC-MSC ACQUIRED USING SAID REAGENT KIT

CROSS-REFERENCE TO RELATED APPLICATION(S)

This application is a National Phase Patent Application of International Patent Application Number PCT/CN2015/097150, filed on Dec. 11, 2015. The entire contents of which are incorporated herein by reference.

TECHNICAL FIELD

The present invention relates to the field of stem cell research. Particularly, the present invention relates to a kit for novel, high efficient serum-free stepwise culture of hUC-MSCs.

BACKGROUND OF THE INVENTION

Mesenchymal stem cells are ubiquitous in many tissues and organs of human body, and have multi-directional differentiation potential. They have functions of stimulating tissue regeneration, and regulating immunity, and have a broad application prospect in the field of cell therapy.

Previous studies show that although bone marrow mesenchymal stem cells have been widely used in clinical, umbilical cord-derived mesenchymal stem cells can not only be ideal substitutes for bone marrow mesenchymal stem cells, but also have a greater potential for application. Human umbilical cord mesenchymal stem cells (hUC-MSCs) derived from human umbilical cord express a variety of special markers for embryonic stem cells, and are characterized by great potential for differentiation, strong proliferative ability, low immunogenicity, convenient material acquisition, having no restrictions on ethical and ethical issues and easy industrialization, etc. Meanwhile, it have been demonstrated in studies that hUC-MSCs have good therapeutic effects in animal models and clinical studies of diseases selected from the group of neurological diseases, the immune system diseases, endocrine system diseases, cancer and heart disease and the like. Thus, hUC-MSCs are possible to be the most clinically promising pluripotent stem cells.

The most important thing to further apply hUC-MSCs to clinic is that, the hUC-MSCs could be expanded abundantly in vitro to reach an effective clinical therapeutic dose. In this regard, culturing hUC-MSCs in vitro has become one of the most fundamental and important technologies. Current medium used in methods for culturing hUC-MSCs is generally basic medium supplemented with FBS, penicillin and streptomycin. However, non-human serum has complex components and may make hUC-MSCs prone to differentiate easily during long-term culture, and there is also a danger of transmitting xenogeneic pathogens by use of non-human serum.

In addition, although various types of serum substitutes have been developed by researchers, cultivation with commercially available serum substitutes and complete culture media for hUC-MSCs is still not ideal, especially, the serum substitutes and complete culture media fail to achieve desired results on adherence and proliferation of stem cells, maintenance of cell stability after long-term culture, and other properties.

SUMMARY OF THE INVENTION

Therefore, one purpose of the present invention is to provide a medium for culturing hUC-MSCs in accordance with the needs of the art, thereby obtaining hUC-MSCs with abilities of good adherence, rapid proliferation and easy differentiation.

Another purpose of the present invention is to provide hUC-MSCs obtained from the medium of the present invention.

Specifically, the present invention provides a novel culture solution for culturing hUC-MSCs with a serum-free stepwise culture kit, and the kit comprises at least two media with different compositions respectively. The stepwise culture and long-term expansion culture of hUC-MSCs can be conducted under serum-free conditions by use of the media in the kit. Meanwhile, the hUC-MSCs can still maintain multipotency and a strong proliferation capacity under condition of long-term culture.

Technical solutions provided by the present invention are as follows.

In one aspect, the present provides a kit for use in stepwise culture of hUC-MSCs, said kit comprises TME medium (i.e., a first medium) and TMD medium (i.e., a second medium which are placed separately. The media both are serum-free and are used for stepwise culture of hUC-MSCs.

The hUC-MSCs are human umbilical cord mesenchymal stem cells isolated from umbilical cord tissue of a healthy newborn by natural or cesarean section delivery. There are various commonly-known methods in the art for separating human umbilical cord mesenchymal stem cells.

In the kit provided by the present invention, the TME medium comprises a-MEM, δ-mercaptoethanol and non-essential amino acids. Preferably, the TME medium comprises 0.05-0.2 parts by volume of β-mercaptoethanol, 0.5-2 parts by volume of aqueous solution of non-essential amino acids, and 90-100 parts by volume of a-MEM, wherein the aqueous solution of non-essential amino acids comprises glycine, alanine, L-asparagine, L-aspartic acid, glutamic acid, proline and serine each at a concentration of 8-12 mM; more preferably, the TME medium comprises 0.1 parts by volume of δ-mercaptoethanol, 1 part by volume of the aqueous solution of non-essential amino acids, and 99 parts by volume of a-MEM; further preferably, the TME medium consists of a-MEM, β-mercaptoethanol and the aqueous solution of non-essential amino acids.

In the kit provided by the present invention, the TMD medium comprises a-MEM/DMEM-F12, β-mercaptoethanol, non-essential amino acids, recombinant human basic fibroblast growth factor (b-FGF) and serum substitute.

Preferably, the TMD medium comprises 0.05-0.2 parts by volume of β-mercaptoethanol, 0.5-2 parts by volume of the aqueous solution of non-essential amino acids, 8-12 parts by volume of the serum substitute, 85-95 parts by volume of a-MEM/DMEM-F12 and the recombinant human basic fibroblast growth factor at a final concentration of 5-15 ng/ml, wherein the aqueous solution of non-essential amino acids comprises glycine, alanine, L-asparagine, L-aspartic acid, glutamic acid, proline and serine each at a concentration of 8-12 mM; more preferably, the TMD medium comprises 0.1 part by volume of β-mercaptoethanol, 1 part by volume of the aqueous solution of non-essential amino acids, 10 parts by volume of the serum substitute, 89 parts by volume of a-MEM/DMEM-F12 and the recombinant human basic fibroblast growth factor at a final concentration of 10 ng/ml. Further preferably the TMD medium consists of a-MEM/DMEM-F12, β-mercaptoethanol, the aqueous solution of non-essential amino acids, recombinant human basic fibroblast growth factor (b-FGF) and serum substitute.

According to particular embodiments of the present application, the aqueous solution of non-essential amino acids can be a product available from Gibco under Catalog No. 11140.

According to particular embodiments of the present application, the serum substitute can be KnockOut™ Serum Replacement (a product available from Gibco under Catalog No. 10828-010).

A method for culturing hUC-MSCs step by step can be performed by use of the present kit, the culture method includes: culturing hUC-MSCs with the TME medium in the kit, and then culturing the hUC-MSCs with the TMD medium in the kit. That is, the two media are used successively to culture hUC-MSCs.

Further, the culture method includes following steps:
(1) inoculating hUC-MSCs into the TME medium in the kit at a density of $0.5\text{-}4\times10^4$ cells/cm$^2$, and culturing the cells for 3-6 hours;
(2) discarding the TME medium, washing the cells with PBS, replacing the PBS with the TMD medium in the kit for further culture, during which the TMD medium is renewed every 3-5 days;
(3) when a confluence of 70-90% is reached, collecting the hUC-MSCs for reserving or cryopreserving, or repeating the step (1) and step (2) for passage to culture.

Optionally, the hUC-MSCs collected in step (3) are taken out to be detected for one or more selected from the group consisting of differentiation ability, cell activity, cell purity, cell contamination and proliferation characteristics.

Preferably, the culture method includes following steps:
(1) inoculating hUC-MSCs into the TME medium in the kit at a density of $2\times10^4$ cells/cm$^2$, and culturing the cells for 3-4 hours;
(2) discarding the TME medium, washing once with PBS, replacing the PBS with the TMD medium in the kit which has been preincubated at 37° C. for further culture, during which the TMD medium is renewed every 3 days;
(3) when a confluence of 90% is reached, collecting the hUC-MSCs for reserving or cryopreserving, or repeating the step (1) and step (2) for passage culture.

Optionally, the hUC-MSCs collected in step (3) are taken out to be detected for one or more selected from the group consisting of differentiation ability, cell activity, cell purity, cell contamination and proliferation characteristics.

According to particular embodiments of the present application, the serum-free stepwise culture method for hUC-MSCs includes following steps:
(1) inoculating hUC-MSCs at a certain density and performing adherent culture in a six-well plate or T75 flask containing the TME medium; preferably, the inoculation density of hUC-MSCs is about $2\times10^4$ cells/cm$^2$;
(2) 4 hours after inoculation, removing and discarding the used medium with a pipettor it, washing once with PBS, and replacing the PBS with the TMD medium in the kit which has been preincubated at 37° C.;
(3) when a confluence of 90% is reached, conducting passage culture according to the above protocol, or cryopreserving the cells.

Optionally, the hUC-MSCs obtained from step (3) can be detected for one or more selected from the group consisting of differentiation ability, cell activity, cell purity, cell contamination and proliferation characteristics.

In another aspect, the present invention also provides hUC-MSCs obtained by the above methods.

Preferably, said hUC-MSCs have the following characteristics:

(1) Adhering to plastic container(s), appearing as spindle-shape and growing in whorls;
(2) Ratio of CD29, CD44, CD73, CD90, CD105 or HLA-ABC positive cells greater than 99%; and ratio of CD45, CD34 or HLA-DR positive cells less than 1.0%;
(3) Capable of being induced to differentiate into osteogenic cells and adipogenic cells in vitro;
(4) Ratio of viable cells detected above 99%;
(5) Having a typical "S type" growth curve; and
(6) Expressing pluripotency genes which are one or more selected from the group consisting of SSEA-4, OCT-4, NANOG and SOX-2.

In yet another aspect, the present invention also provides TME medium and/or TMD medium used in the above culture methods.

The TME medium and TMD medium in the kit of the present invention are serum-free with a clear composition, thereby avoiding the instability of the cell growth during the culture due to batch difference of the serum, and also excluding the possibility of spreading xenogeneic pathogens.

In addition, the problems of poor adherence and slow proliferation of cells in conventional serum-free culture can be solved successfully by conducting stepwise culture using the two media in the kit, i.e. promoting adherence of hUC-MSCs by use of the TME medium, and conducting rapid proliferation by use of the TMD medium. What's more, the hUC-MSCs cultured can maintain good proliferation and multi-directional differentiation potential during long-term culture, thereby providing an efficient solution for animal cell culture in vitro.

Moreover, operation with the kit of the present invention is simple and easy, and shortens the time for the primary culture.

Results of flow cytometry detection, viability determination, differentiation identification and pluripotency gene analysis have shown that the mesenchymal stem cells prepared by the method of present invention have high viability and purity, and strong differentiation capability, and the cell bank established with the stem cells can be directly utilized in scientific research and clinical adjuvant treatment.

BRIEF DESCRIPTION OF THE DRAWINGS

Hereinafter, embodiments of the present invention will be described with reference to the accompanying drawings in detail, in which.

DETAILED DESCRIPTION OF PREFERRED EMBODIMENTS

The present invention will be further described in detail in combination with the embodiments hereinafter. It will be appreciated by those skilled in the art that the embodiments provided are only used to illustrate the present invention, rather than limiting the scope of the present invention in any way.

Experimental methods in the following embodiments, if no any other special instruction is provided, are all conducted under conventional conditions or the conditions recommended by the instrument and reagent supplier. Materials used in the following examples, if no source of purchase is provided, are conventional products that can be commercially available.

Example 1: Culturing hUC-MSCs with Conventional Medium Containing Serum

Medium to be tested: 89 parts by volume of a-MEM, 10% fetal calf serum (FBS), 100 U/ml of penicillin, 100 U/ml streptomycin, 0.1 part by volume of β-mercaptoethanol, 10 ng/ml b-FGF, and 1 part by volume of aqueous solution of non-essential amino acids (11140, Gibco).

In a biosafety cabinet, the third generation hUC-MSCs isolated from Wharton's jelly tissue of umbilical cord of a newborn by natural delivery were inoculated into a T75 cell culture flask at a density of $2 \times 10^4$ cells/cm$^2$, then the flask was transferred to a constant temperature incubator at 37° C., 5% $CO_2$ after 15 ml of the medium to be tested was added in. Cell adhesion observed 2 hours after inoculation showed that a large amount of hUC-MSCs adhered to the walls of the flask and had tentacles stretched out; and more than 90% confluence was reached when observed 48 hours after inoculation; and the hUC-MSCs were bright and had tentacles in stretched state.

Figure 1:
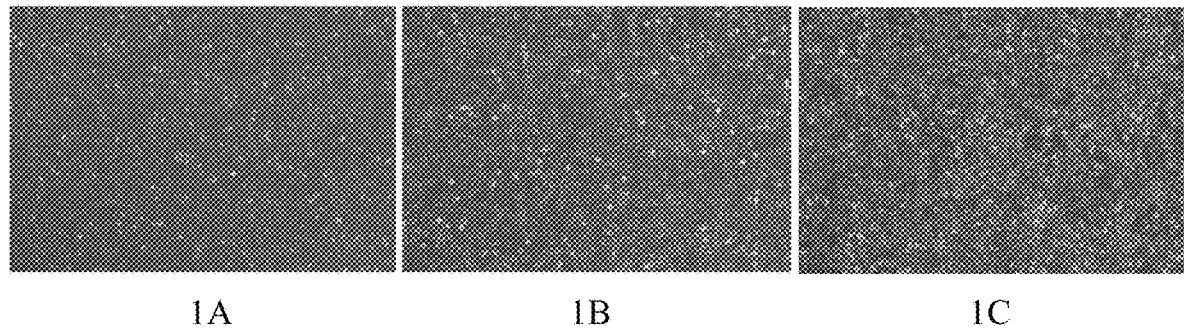
FIG. 1 shows images of culturing hUC-MSCs by use of a medium comprising serum, in which panel 1A shows cell morphology 2 hours after inoculation, panel 1B shows cell morphology 24 hours after inoculation, and panel 1C shows cell morphology 48 hours after inoculation.
Figure 2:
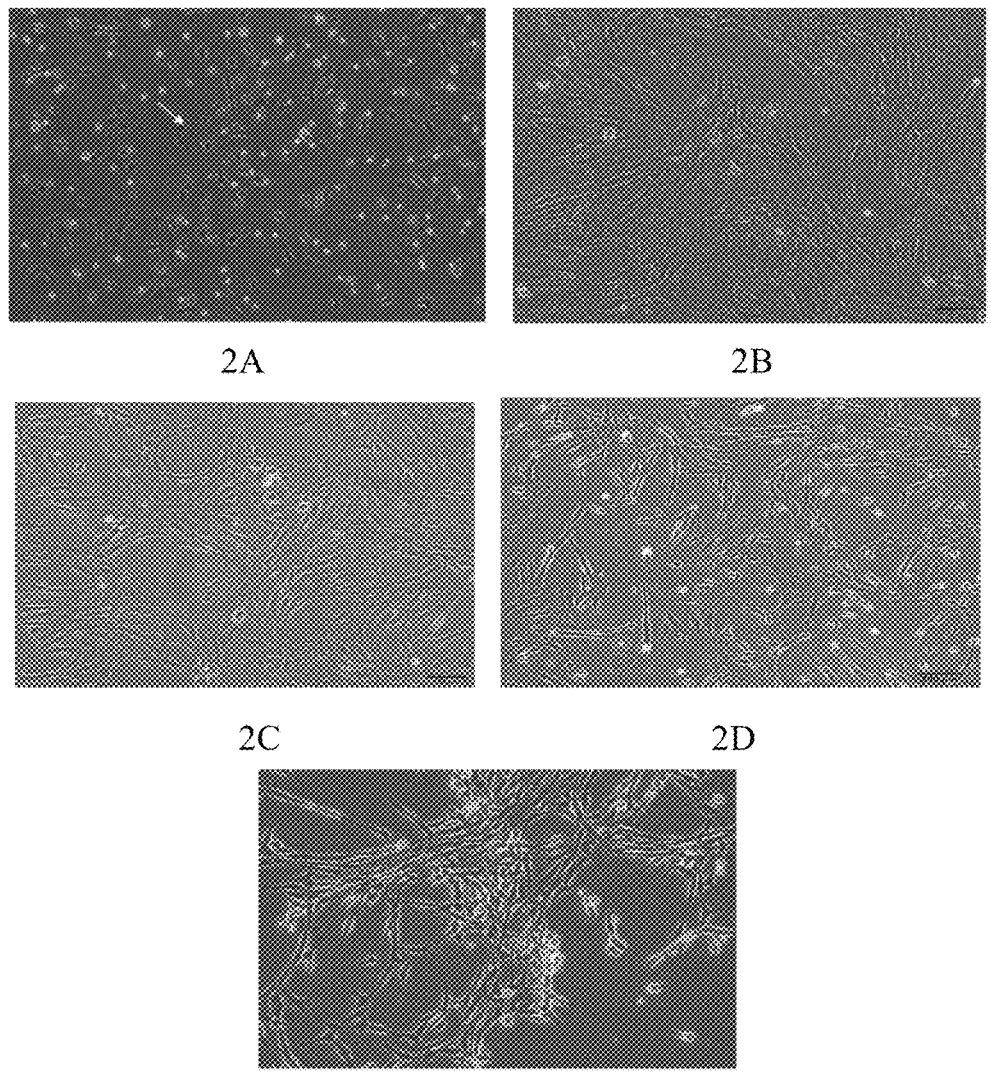
FIG. 2 shows cell images during the screening of medium components, in which panel 2A shows cell morphology 4 hours after cells were inoculated in a medium comprising a high concentration of β-mercaptoethanol, panel 2B shows cell morphology 48 hours after cells were inoculated in a medium comprising a low concentration of serum substitute, panel 2C shows cell morphology 24 hours after cells were inoculated in a medium comprising a high concentration of serum substitute, panel 2D shows cell morphology 24 hours after cells were inoculated in medium comprising a low concentration of bFGF, and panel 2E shows cell morphology after cells were passaged in a culture medium comprising a high concentration of bFGF.

See FIG. 1 for cell morphology. However, during the culture of cells, there is a possibility of spreading xenogeneic pathogens by incorporating serum, and the batch difference of the serum may also lead to the instability of the cell growth.

Example 2: Culturing hUC-MSCs with Conventional and Commercially Available Serum-Free Medium With reference to the method as described in Example 1, cells from the same cell source were inoculated at the same density, and cultured with addition of 15 ml of commercially available serum-free medium (Cyagen, HUXUC-90061). The cells were observed to have adhered to the walls of the flask 2 hours after inoculation, which were bright and round, and had tentacles in stretched state; and 24 hours after inoculation, bright hUC-MSCs which had stretched tentacles and unobvious expansion could be observed under a microscope. A confluence of about 50% could be reached by the cells 48 hours afterf inoculation; and observation 72 hours after inoculation showed that the hUC-MSCs were bright and more than 90% confluence was reached. The cells were digested by trypsin, collected and cryopreserved.

Optionally, the cells were continuously cultured after a confluence of 100% was reached; however, the cells began to curl and fall off from the edge of the flask. It can be seen that the cells are prone to fall off easily and can not maintain a good adherent state.

Example 3: Screening for the Composition of the Medium (i) Screening for the Composition of the TME Medium Medium to be tested: 0.01, 0.02, 0.05, 0.1, 0.15, 0.2, 0.3 or 0.5 part by volume of β-mercaptoethanol, 1 part by volume of aqueous solution of non-essential amino acids (11140, Gibco), and 99 parts by volume of a-MEM.

With reference to the method as described in Example 1, cells from the same cell source were inoculated at the same density, then 12-15 ml of the medium to be tested was added in and theadherence of the cells was observed.

Results: The cells in the two concentration groups, i.e. the medium comprising 0.01 or 0.02 part by volume of β-mercaptoethanol respectively adhered to the walls at a slower rate. Some of the cells still did not adhere to the walls 4 hours after inoculation and nearly all the cells were observed to have adhered about 8 hours after inoculation. The cells in the four concentration groups, i.e. the medium comprising 0.05, 0.1, 0.15 or 0.2 parts by volume of β-mercaptoethanol respectively adhered to the walls completely 4 hours after inoculation, and bright cells with tentacles stretched out were observed. The cells in the two concentration groups, i.e. the medium comprising 0.3 or 0.5 part by volume of β-mercaptoethanol respectively had adhered to the walls 4 hours after inoculation, but some of the cells were in poor state and showed symptoms of early differentiation (see panel 2A).

(ii) Screening for the Composition of the TMD Medium

TME medium: 0.1 part by volume of β-mercaptoethanol, 1 part by volume of aqueous solution of non-essential amino acids (11140, Gibco), and 99 parts by volume of a-MEM.

Medium to be tested: 0.1 parts by volume of β-mercaptoethanol, 10 ng/ml recombinant human basic fibroblast growth factor (b-FGF, Peprotech), 1 part by volume of aqueous solution of non-essential amino acids (11140, Gibco), 1, 2, 5, 8, 10, 12, 15, or 20 parts by volume of Knockout FBS serum substitute (Catalog No. 10828-028, Gibco), and 89 parts by volume of a-MEM.

With reference to the method as described in Example 1, the cells from the same source were inoculated at the same density, and cultured in 15 ml TME medium. The cells were observed to have adhered 2 hours after inoculation. Cultured continuously, the cells were observed to have completely adhered 4 hours after inoculation, then the medium was replaced with 15 ml of the medium to be tested. The growth of the cells was observed.

Results: The cells in the three concentration groups, i.e. the medium comprising 1, 2 or 5 parts by volume of serum substitute respectively proliferated slowly, and 24 hours after inoculation, it was observed that part of the hUC-MSCs gathered while the cells were flat with poor refractive index and about 20% confluence; and subsequent observation 48 hours after inoculation showed that the hUC-MSCs were bright but the proliferation almost stopped when 60% confluence was reached (see panel 2B). However, the cells in the three concentration groups, i.e. the medium comprising 8, 10 or 12 parts by volume of serum substitute respectively were in good growth state, and 24 hours after inoculation, it was observed that the hUC-MSCs appeared as spindle-shape and gathered in whorls spreading much more, and the cells were bright, and 40-60% confluence was reached; and subsequent observation 48 hours after inoculation showed that the hUC-MSCs were bright and more than 90% confluence was reached. Similar to those in the low concentrations of serum substitute, the cells proliferated slowly in the two concentration groups, i.e. the medium comprising 15 or 20 parts by volume of serum substitute respectively, and the cells were flat with a clear outline (see panel 2C).

(iii) Screening for the Composition of the TMD Medium

TME medium: 0.1 part by volume of β-mercaptoethanol, 1 part by volume of aqueous solution of non-essential amino acids (11140, Gibco), and 99 parts by volume of a-MEM.

Medium to be tested: 0.1 parts by volume of β-mercaptoethanol, 1, 2, 5, 8, 10, 12, 15, 18, or 20 ng/ml recombinant human basic fibroblast growth factor (b-FGF, Peprotech), 1 part by volume of aqueous solution of non-essential amino acids (11140, Gibco), 10 parts by volume of Knockout FBS serum substitute (Catalog No. 10828-028, Gibco), and 89 parts by volume of a-MEM.

With reference to the method as described in Example 1, the cells from the same source were inoculated at the same density, and cultured in 15 ml TME medium. The cells were adherent when observed 2 hours after inoculation. Cultured continuously, the cells were observed to have completely adhered 4 hours after inoculation, then the medium was replaced with 15 ml of the medium to be tested. The growth of the cells was observed.

Results: The cells in the two concentration groups, i.e. medium comprising 1 or 2 ng/ml bFGF respectively proliferated slowly and were in poor and undernourished state (see panel 2D). In the concentration groups, i.e. the medium comprising 5, 8, 10, 12 or 15 ng/ml bFGF respectively, the cells grew normally, and had high brightness and good growth state. In the concentration groups, i.e. the medium comprising 18 or 20 ng/ml bFGF respectively, well proliferating and bright cells could be observed. However, the cells were prone to differentiate, clustered into a mass, or had longer tentacles after several passages (see panel 2E).

Example 4: Culturing hUC-MSCs by Utilizing the TME Medium in the Kit

TME medium: 0.1 part by volume of β-mercaptoethanol, 1 part by volume of aqueous solution of non-essential amino acids (11140, Gibco), and 99 parts by volume of a-MEM.

In a biosafety cabinet, the third generation hUC-MSCs isolated from Wharton's jelly tissue of umbilical cord of a newborn by natural delivery were inoculated into a T75 cell culture flask at a density of $2\times10^4$ cells/cm$^2$, then the flasks was transferred to a constant temperature incubator at 37° C., 5% $CO_2$ after 15 ml of the TME medium was added in. 2 hours After inoculation, the cells were observed to have adhered and have stretched out tentacles. The flask was removed out of the incubator 24 hours and 48 hours after inoculation respectively, and the cells therein were observed to adhere well but proliferate unobviously and a large number of floating dead cells appeared. On the $3^{th}$ day after inoculation, the cells were further cultured with the replaced fresh TME medium, and gradually fell off from the bottom of the flask and died. The proliferation of the cells was unobvious.

Figure 3:
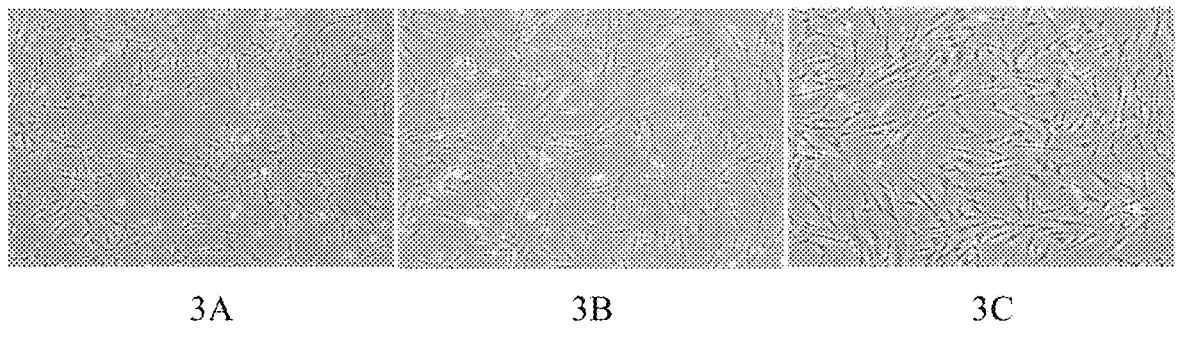
FIG. 3 shows images of culturing hUC-MSCs by use of the TME medium in the kit, in which panel 3A shows cell morphology 2 hours after inoculation, panel 3B shows cell morphology 24 hours after inoculation, and panel 3C shows cell morphology 48 hours after inoculation.

See FIG. 3 for cell morphology.

Example 5: Culturing hUC-MSCs by Utilizing the TMD Medium in the Kit

TMD medium: 0.1 part by volume of β-mercaptoethanol, 10 ng/ml recombinant human basic fibroblast growth factor (b-FGF, Peprotech), 1 part by volume of aqueous solution of non-essential amino acids (11140, Gibco), 10 parts by volume of Knockout FBS serum substitute (Catalog No. 10828-028, Gibco), and 89 parts by volume of a-MEM.

With reference to the method as described in Example 4, the cells from the same source were inoculated at the same density, and cultured in 15 ml TMD medium. Similarly, Cell adhesion observed 2 hours after inoculation showed that a large amount of hUC-MSCs were unadhered and floating in the medium. The cells adhered to the walls non-uniformly and aggregated locally when observed 24 hours after inoculation. And adherent hUC-MSCs and a larger area of aggregation were observed 48 hours after inoculation; on the $3^{th}$ day after inoculation, the cells were further cultured with the replaced fresh TMD medium, and some of them fell off during changing the medium and a small number of them were aging or dying. 96 hours after inoculation, about 90% confluence was reached.

Figure 4:
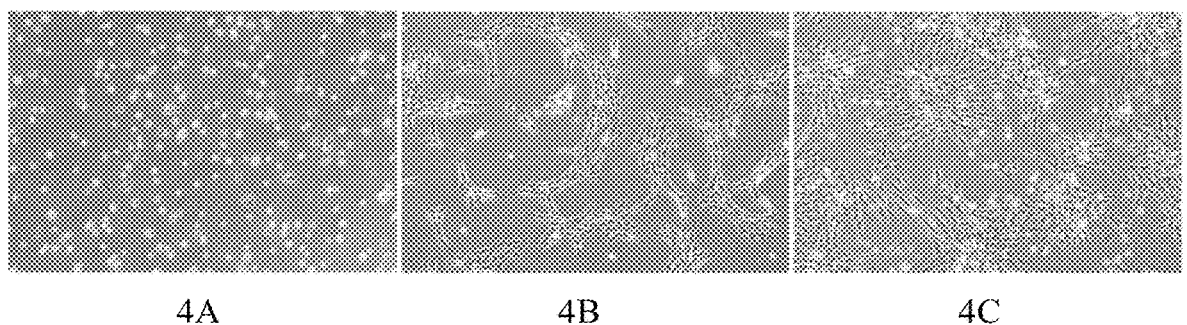
FIG. 4 shows images of culturing hUC-MSCs by use of the TMD medium in the kit, in which panel 4A shows cell morphology 2 hours after inoculation, panel 4B shows cell morphology 24 hours after inoculation, and panel 4C shows cell morphology 48 hours after inoculation.

See FIG. 4 for cell morphology.

Example 6: The Serum-Free Stepwise Cultivation of hUC-MSCs by Utilizing the Present Kit TME medium: 0.1 part by volume of β-mercaptoethanol, 1 part by volume of aqueous solution of non-essential amino acids (11140, Gibco), and 99 parts by volume of a-MEM.

TMD medium: 0.1 part by volume of β-mercaptoethanol, 10 ng/ml recombinant human basic fibroblast growth factor (b-FGF, Peprotech), 1 part by volume of aqueous solution of non-essential amino acids (11140, Gibco), 10 parts by volume of Knockout FBS serum substitute (Catalog No. 10828-028, Gibco), and 89 parts by volume of a-MEM.

With reference to the method as described in Example 4, the cells from the same source were inoculated at the same density, and cultured in 15 ml TME medium. The cells were adherent when observed 2 hours after inoculation; then, they were cultured continuously and were observed to have completely adhered 4 hours after inoculation. Then the medium was replaced with fresh TMD medium, and 24 hours after inoculation, it was observed that the hUC-MSCs appeared as spindle-shape and gathered in whorls spreading much more, and the cells were bright, and 40-60% confluence was reached. Subsequent observation 48 hours after inoculation showed that the hUC-MSCs were bright and more than 90% confluence was reached. Then the cells were digested by trypsin, collected and cryopreserved.

Optionally, the cells were continuously cultured after a confluence of 100% was reached, and no cells were observed to have fallen off, and all the cells can maintain a good adherent state for a long time.

Figure 5:
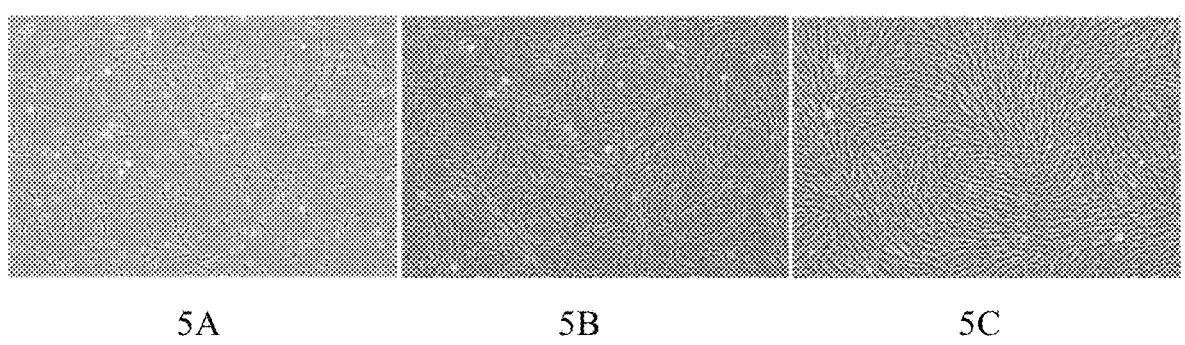
FIG. 5 shows images of culturing hUC-MSCs step by step by use of the present kit, in which panel 5A shows cell morphology 2 hours after inoculation by use of the TME medium in the kit, panel 5B shows cell morphology of cells which were inoculated in the TME medium and cultured for 4 hours and then further cultured for 24 hours after replacement of the TME medium with the TMD medium, and panel 5C shows cell morphology of cells which were inoculated in the TME medium and cultured for 4 hours and then further cultured for 48 hours after replacement of the TME medium with the TMD medium.

See FIG. 5 for cell morphology.

Comparing with Example 6 with Example 1, the serum-free stepwise culture by use of the TME medium and TMD medium achieves the same results as conventional serum culture, and at the same time, the possibility of spreading xenogeneic pathogens by incorporating of serum is excluded, and also the instability of the cell growth during the culture due to batch difference of the serum is avoided.

Example 7: Analysis of Surface Markers of the Huc-MSC by Flow Cytometry

The third generation cells cultured in Example 6 were digested by 2 mL 0.125% trypsin when 90% confluence was reached, and then centrifuged at 1200 rpm for 6 minutes at 4° C. The supernatant was discarded and the cells were collected and washed twice with PBS. The cells were then transferred to a flow tube in an amount of $1\times10^5$ cells per tube, and 5 μL of each of CD34-PE, CD45-FITC, CD29-FITC, CD44-PE, CD73-PE, CD105-PE, CD90-FITC, HLA-ABC-FITC, HLA-DR-PE, IgG1-PE (isotype control), and IgG1-FITC (isotype control) antibodies was added into the tube respectively. The cells were mixed and incubated in dark for 30 minutes at 4° C., washed once with PBS, centrifuged and the supernatant was discarded. The collected cells were resuspended by addition of 500 μL PBS, and then detected on a Flow Cytometer (Flow Cytometer XL, Beckman). $1\times10^4$ cells were collected from each sample.

Figure 6:
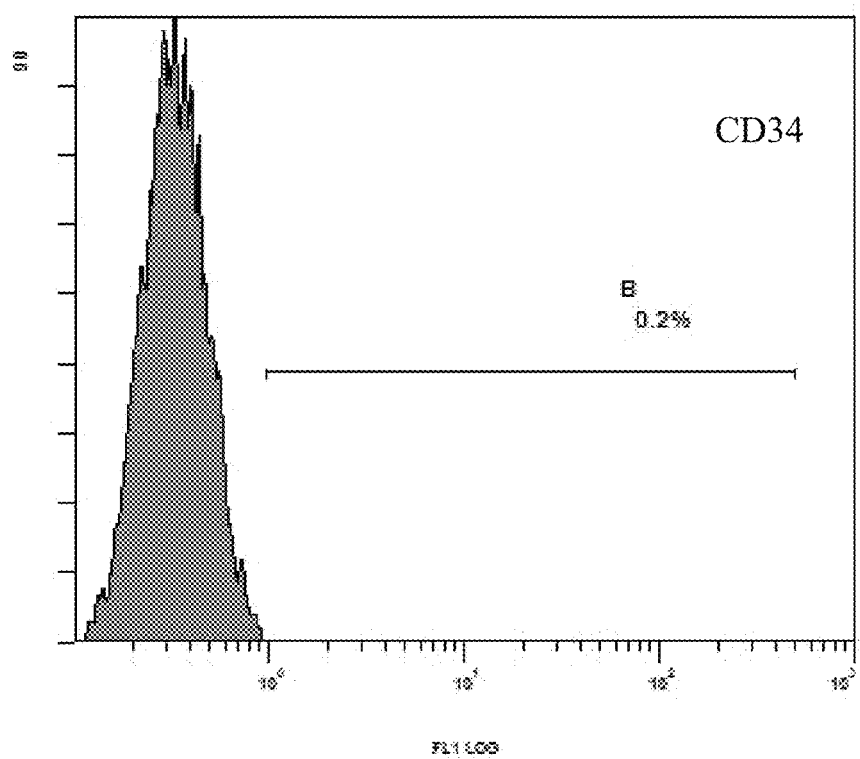
FIG. 6 (panels 6A to 6I) shows the flow cytometry analysis results of cell surface molecules of the hUC-MSCs obtained by conducting serum-free stepwise culture, indicating that the hUC-MSCs expressed CD29, CD44, CD73, CD90, CD105 and HLA-ABC with ratios of positive cells greater than 99.0%, and the hUC-MSCs expressed CD45, CD34 and HLA-DR with ratios of positive cells less than 1.0%.
Figure 6:
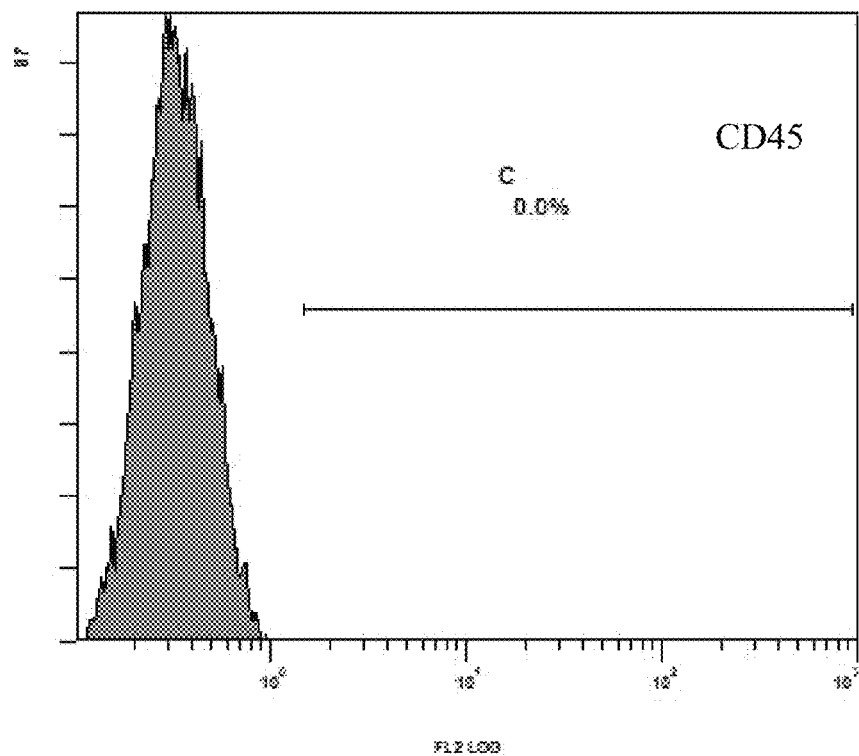
Figure 6:
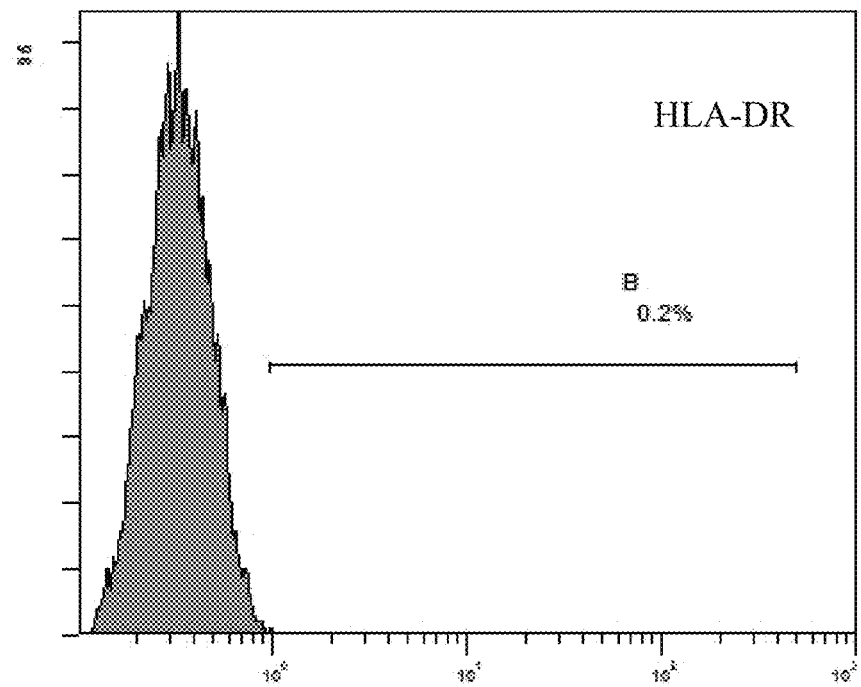
Figure 6:
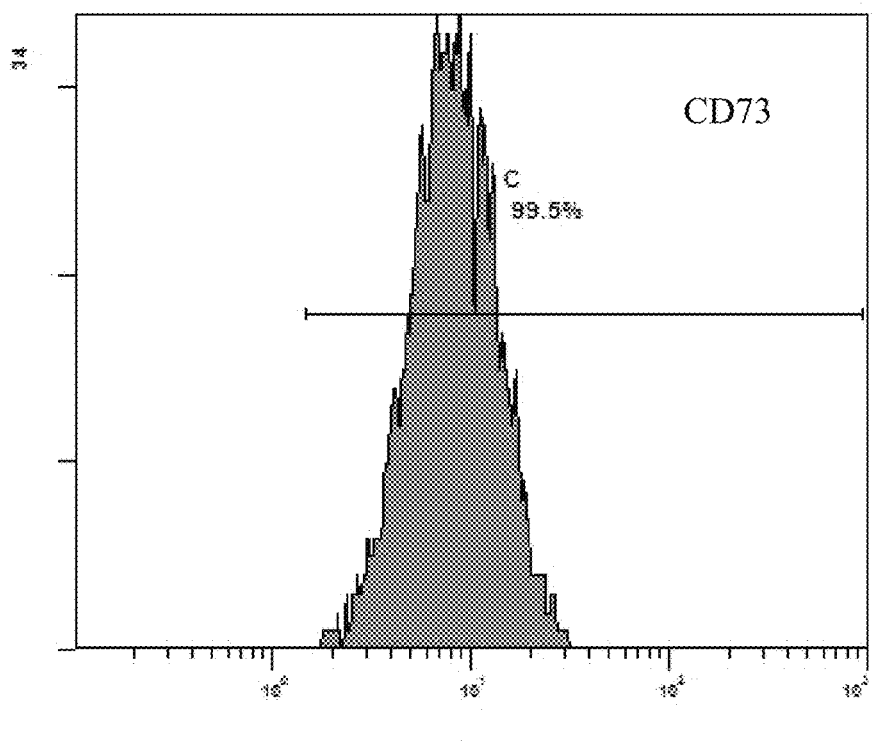
Figure 6:
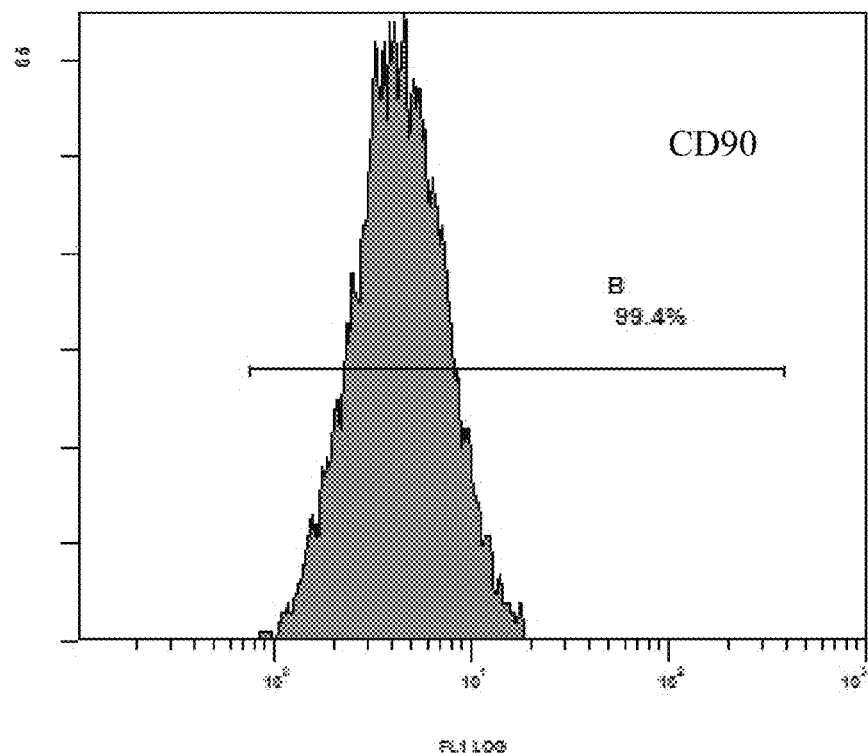
Figure 6:
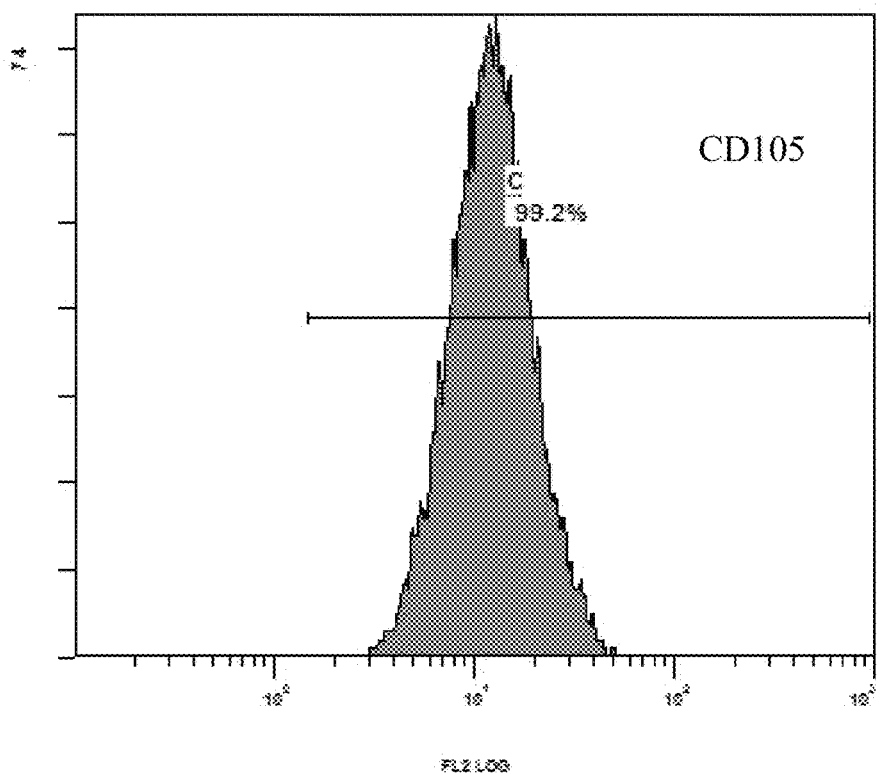
Figure 6:
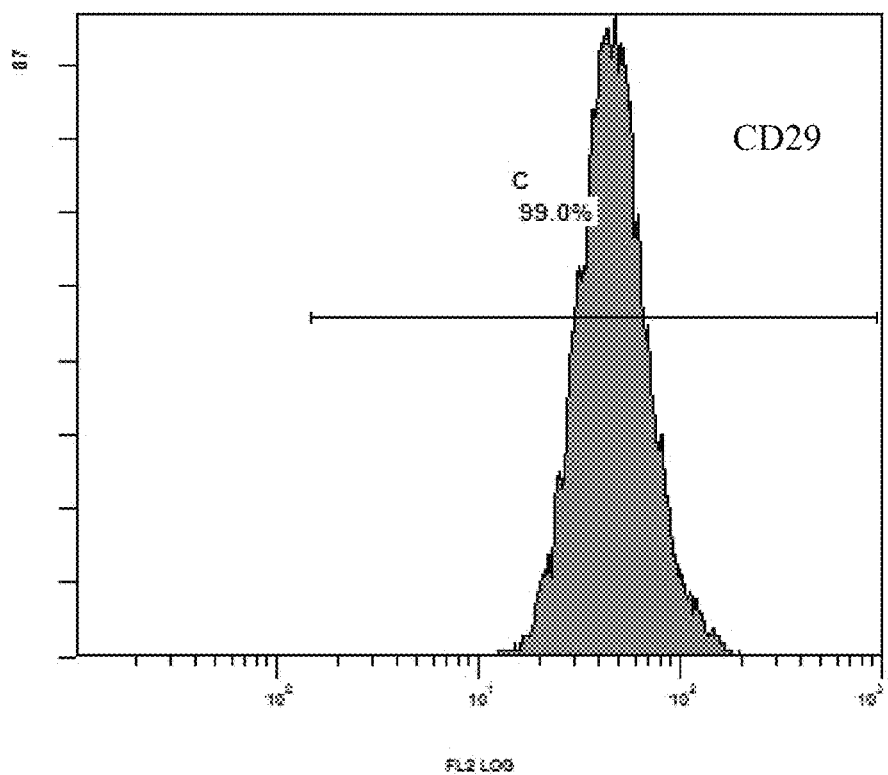
Figure 6:
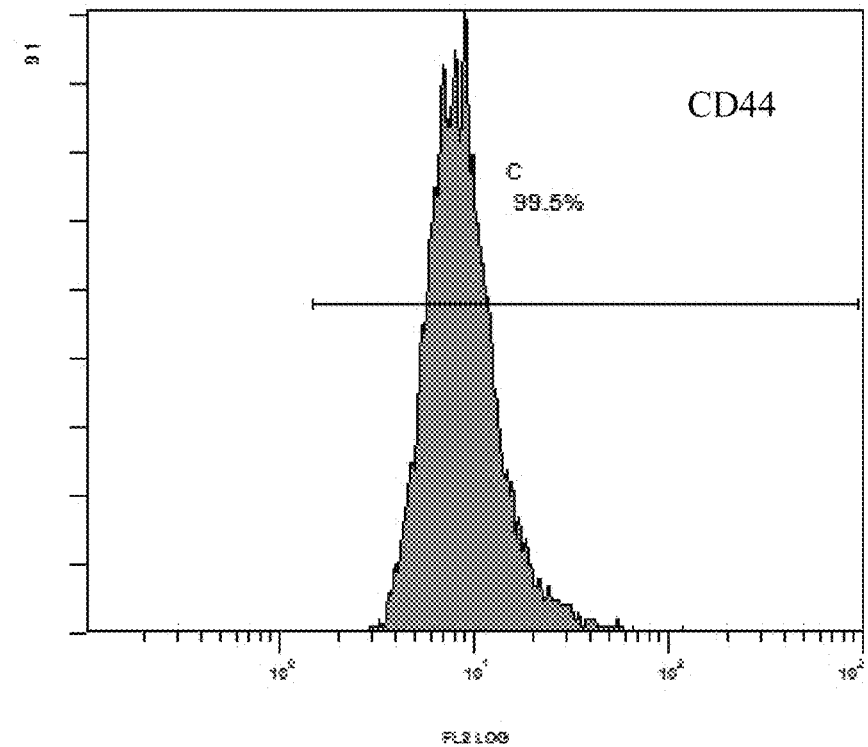
Figure 6:
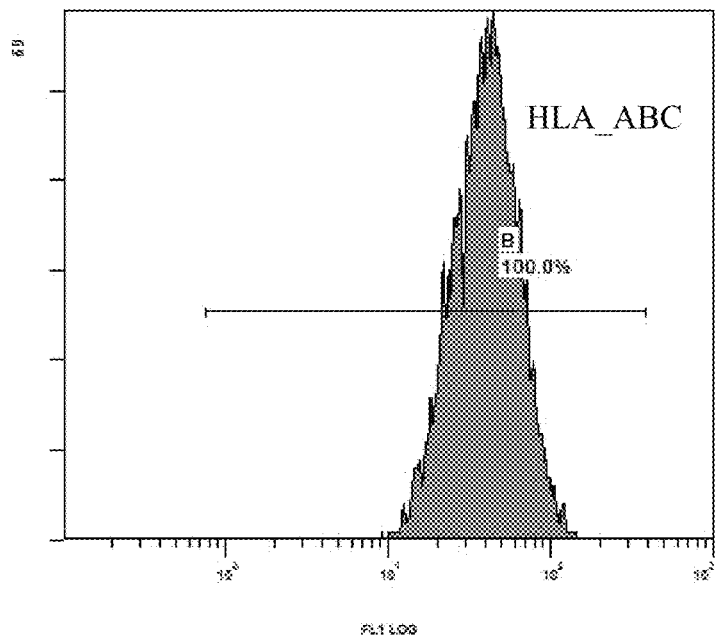

See FIG. 6 for results.

Example 8: Analysis of Cell Viability and Growth Characteristics of hUC-MSCs by Cell Viability Analyzer The third generation cells cultured in Example 6 were inoculated into a T25 culture flask, and when 95%-100% confluence was reached, the cells were digested by 0.125% trypsin, collected and inoculated into two 6-well plates at a density of $1\times10^5$ cells/cm². After all the cells had adhered and partially grown for 10 hours, cells in two wells were collected and prepared into a cell suspension by addition of 500 μL of PBS which was then analyzed on a cell viability analyzer (Cell Viability Analyzer Vi-Cell XR, Beckman). After that, sampling and analysis were conducted every 12 hours and growth curve was drawn accordingly.

Figure 7:
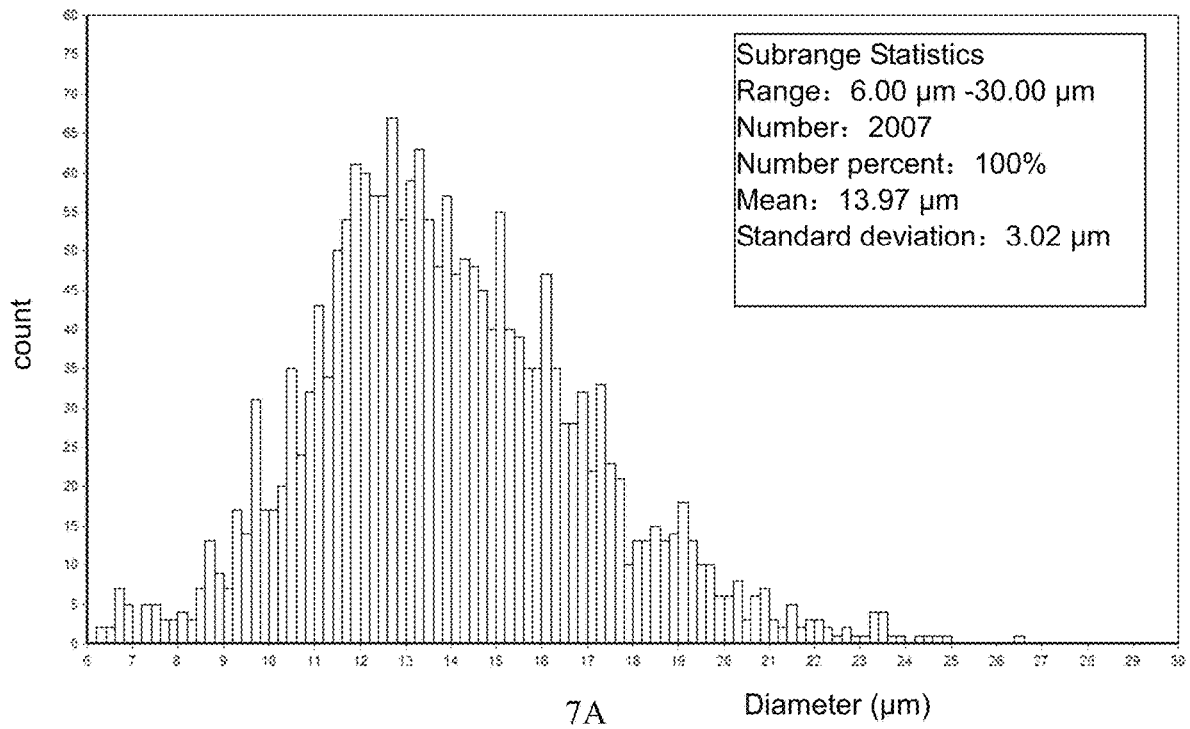
FIG. 7 shows the analysis results of the cell viability and growth profile of the obtained hUC-MSCs by Vi-Cell cell vitality analyzer, in which panel 7A shows the diameter distribution of the hUC-MSCs, panel 7B shows the growth curve of the hUC-MSCs, and panel 7C shows the real-time viability analysis of the hUC-MSCs. The results indicated that the viability of the hUC-MSCs was above 99.7% with a diameter distribution of about 13 μm, and the hUC-MSCs had proliferation profile characterized by latent stage, logarithmic growth stage and platform stage.
Figure 7:
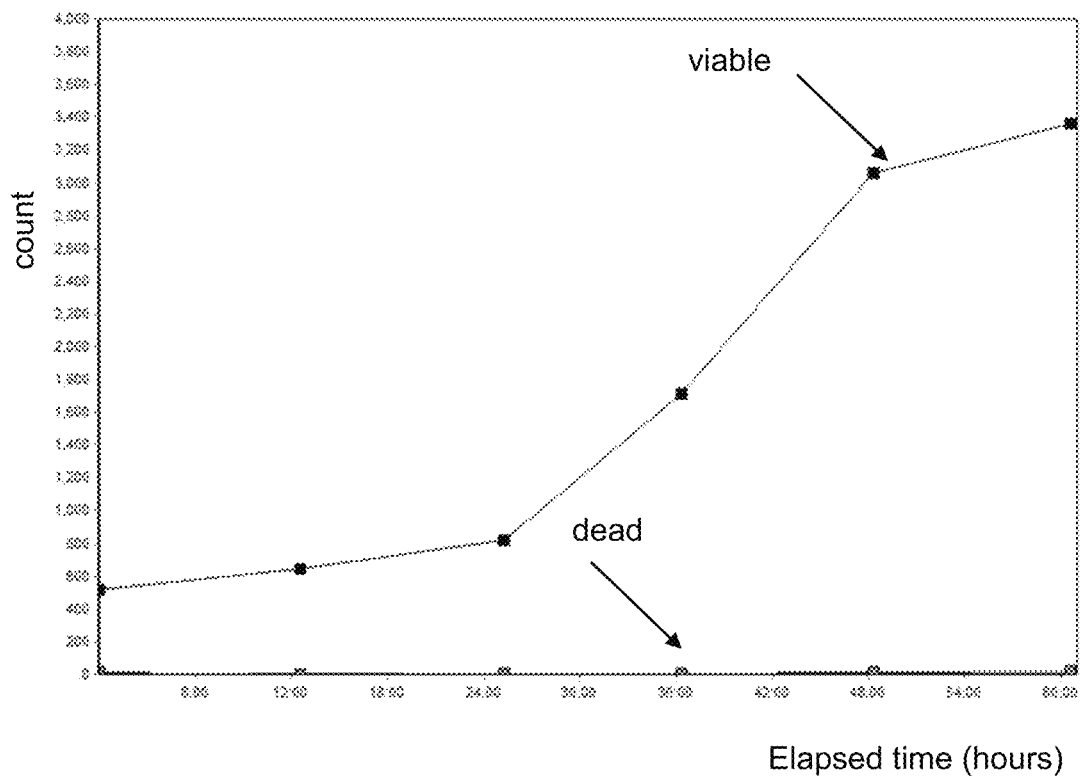
Figure 7:
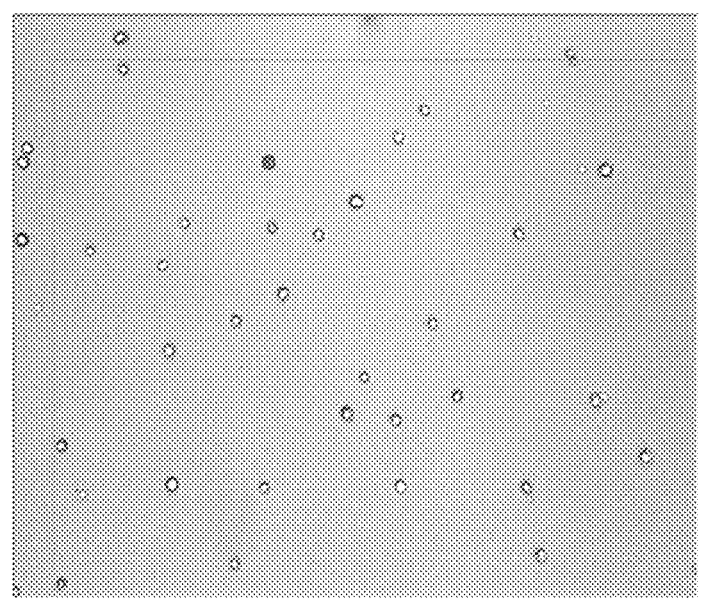
Figure 8:
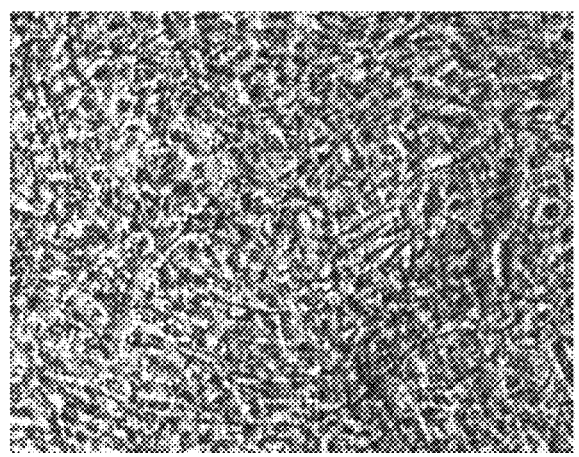
FIG. 8 shows the directed induced differentiation of the obtained hUC-MSCs into osteogenic cells and adipogenic cells, in which panel 8A shows dark red compounds produced by chromogenic reaction between alizarin red and calcium nodules during osteogenesis, and panel 8B shows the specific oil red O staining of the fat droplets in adipogenic cells.
Figure 8:
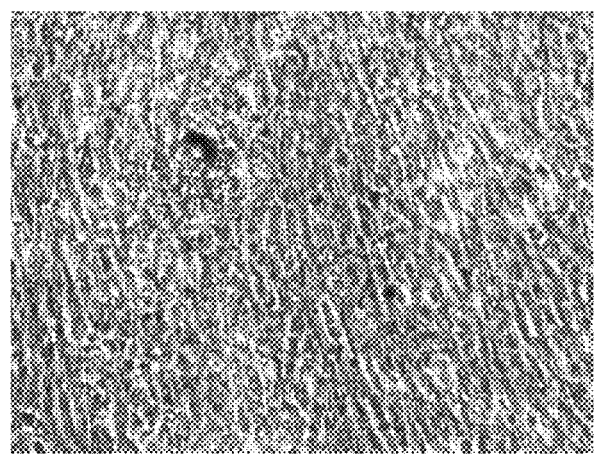

Results shown in FIG. 7 indicated that the viability of hUC-MSCs was above 99.7% and the cell diameter distribution was around 9-15 μm. Meanwhile the cells had proliferation characteristics of latent period, logarithmic growth period and plateau period.

Example 9: Identification of Multi-Directional Differentiation Potential of the hUC-MSCs 1) Osteogenic Differentiation The third generation hUC-MSCs cultured in Example 6 were inoculated into a 6-well cell culture plate at a density of $3\times10^4$ cells/cm², 2 ml of freshly prepared human UC MSC osteogenic differentiation medium (HUXUC-90021, Cyagen) was added into per well after 24 hours, and the medium was replaced with fresh osteogenic differentiation medium every 3 days thereafter. Two weeks later, the cells were fixed with paraformaldehyde, and stained with alizarin red for 3-5 minutes.

The results shown in panel 8A indicated that after two weeks of osteogenic induction on hUC MSCs obtained by culture with the medium of present invention, a dark red chromogenic reaction between the alizarin red and calcium nodules during osteogenesis took place.

2) Adipogenic Differentiation

The third generation cells cultured in Example 6 were inoculated into a 6-well cell culture plate at a density of $2\times10^4$ cells/cm². When 100% confluence had reached, fresh liquid A of adipogenic differentiation medium (HUXUC-90031, Cyagen) was added to each well to start induction. Three days later, the liquid A was replaced with liquid B of adipogenic differentiation medium and the culture was maintained for 24 hours. So the cycle continued until more but fairly small fat droplets appeared, then the culture system was maintained for 7 day with liquid B of adipogenic differentiation medium. When the induction ended, the cells were fixed with 4% paraformaldehyde and stained with Oil red O.

The results shown in penal 8B indicated that the adipogenic cells were stained significantly by Oil red O after two weeks of adipogenic induction on hUC-MSCs obtained by the method of present invention.

Example 10: Immunofluorescence Staining Analysis of hUC-MSCs Specific Protein The fifth generation hUC-MSCs cultured in Example 6 were inoculated into a 24-well cell culture plate at a density of $5\times10^3$ cells/cm². When 30%-50% confluence was reached, the cells were fixed with 4% paraformaldehyde for 15 minutes, and permeabiliz with 0.25% TritonX-100 for 20 minutes. Goat serum was used for blocking, pre-diluted mouse anti-human primary antibody (anti-SOX2 antibody, anti-OCT4 antibody, anti-NANOG antibody or anti-NANOG antibody) was added, and then the cells were incubated in dark over night at 4° C. Thereafter, FITC labled goat anti-mouse secondary antibody was added and the cells were incubated in dark for 2 hours under room temperature.

Nuclei of the cells were stained with DAPI/PI, and incubated in dark for 20 minutes under room temperature.

Figure 9:
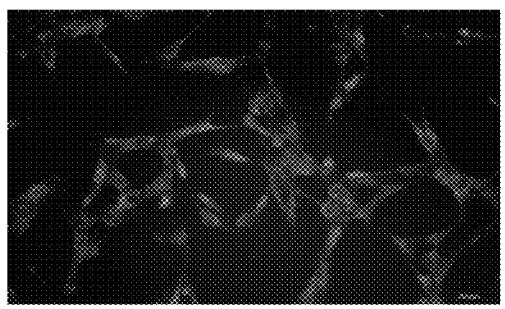
FIG. 9 shows the immunofluorescence staining analysis result of the pluripotency specific proteins of hUC-MSCs, and from left to right and top to bottom, the panels show SSEA-4, SOX-2, OCT-4, and NANOG in order.
Figure 9:
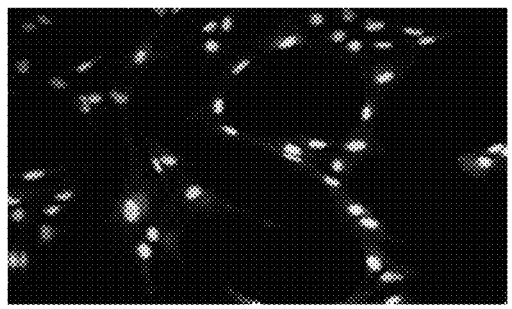
Figure 9:
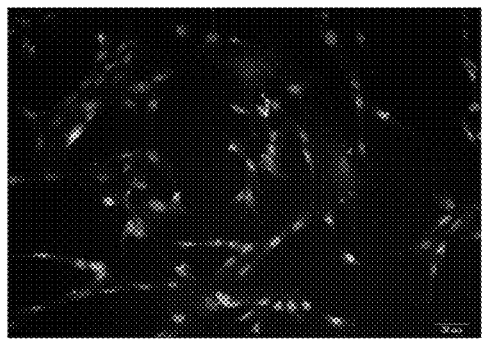
Figure 9:
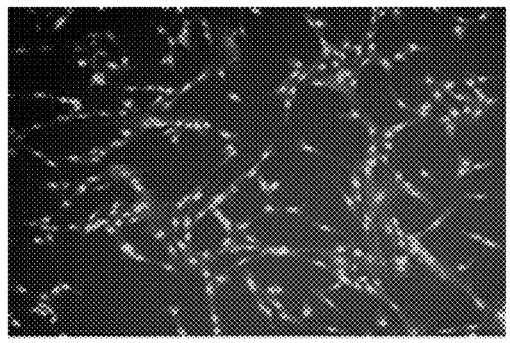

The results shown in FIG. 9 indicated that hUC-MSCs cultured by the stepwise method of the present invention expressed SOX-2, OCT-4, NANOG and SSEA-4 specific proteins.

The above description for the embodiments of the present invention is not intended to limit the present invention, and those skilled in the art can make various changes and variations according to the present invention, which are within the protection scope of the present invention without departing from the spirit of the same.

What is claimed is:

1. A kit for use in stepwise culture of hUC-MSCs, comprising a first medium and a second medium which are placed separately,
wherein the first medium consists of 90-100 parts by volume of a-MEM, 0.05-0.2 parts by volume of β-mercaptoethanol and 0.5-2 parts by volume of aqueous solution of non-essential amino acids, and wherein in the first medium, the aqueous solution of non-essential amino acids comprises glycine, alanine, L-asparagine, L-aspartic acid, glutamic acid, proline and serine, each at a concentration of 8-12 mM, and
the second medium consists of 85-95 parts by volume of a-MEM or DMEM-F12, 0.05-0.2 parts by volume of β-mercaptoethanol, 0.5-2 parts by volume of aqueous solution of non-essential amino acids, recombinant human basic fibroblast growth factor (b-FGF) at a final concentration of 5-15 ng/ml and 8-12 parts by volume of serum substitute, and wherein in the second medium, the aqueous solution of non-essential amino acids comprises glycine, alanine, L-asparagine, L-aspartic acid, glutamic acid, proline and serine, each at a concentration of 8-12 mM.

2. The kit according to claim 1, wherein the hUC-MSCs are human umbilical cord mesenchymal stem cells isolated from umbilical cord tissue of a healthy newborn by natural or cesarean section delivery.

3. The kit according to claim 1, wherein
the first medium consists of 0.1 parts by volume of β-mercaptoethanol, 1 part by volume of the aqueous solution of non-essential amino acids, and 99 parts by volume of a-MEM.

4. The kit according to claim 1, wherein the second medium consists of 0.1 part by volume of β-mercaptoethanol, 1 part by volume of the aqueous solution of non-essential amino acids, 10 parts by volume of the serum substitute, 89 parts by volume of a-MEM or DMEM-F12 and the recombinant human basic fibroblast growth factor at a final concentration of 10 ng/ml.

5. A method of culturing hUC-MSCs using the kit according to claim 1, wherein the method includes: culturing hUC-MSCs with the first medium in the kit, and then culturing the hUC-MSCs with the second medium in the kit.

6. The method according to claim 5, wherein the method includes following steps:
(1) inoculating hUC-MSCs into the first medium at a density of $0.5$-$4 \times 10^4$ cells/cm$^2$, and culturing the cells for 3-6 hours;
(2) discarding the first medium, washing the cells with PBS, replacing the PBS with the second medium for further culture, during which the second medium is renewed every 3-5 days;
(3) when a confluence of 70-90% is reached, collecting the hUC-MSCs for preserving or cryopreserving, or repeating the step (1) and step (2) for passaging;
optionally, the hUC-MSCs collected in step (3) are used for determining one or more selected from the group consisting of differentiation ability, cell activity, cell purity, cell contamination and proliferation characteristics.

7. The method according to claim 5, wherein the method includes following steps:
(1) inoculating hUC-MSCs into the first medium at a density of $2 \times 10^4$ cells/cm$^2$, and culturing the cells for 3-4 hours;
(2) discarding the first medium, washing once with PBS, replacing the PBS with the second medium which has been preincubated at 37° C. for further culture, during which the second medium is renewed every 3 days;
(3) when a confluence of 90% is reached, collecting the hUC-MSCs for preserving or cryopreserving, or repeating the step (1) and step (2) for passaging;
optionally, the hUC-MSCs collected in step (3) are used for determining one or more selected from the group consisting of differentiation ability, cell activity, cell purity, cell contamination and proliferation characteristics.

* * * * *